United States Patent [19]

Lennox et al.

[11] Patent Number: 5,405,322
[45] Date of Patent: Apr. 11, 1995

[54] METHOD FOR TREATING ANEURYSMS WITH A THERMAL SOURCE

[75] Inventors: Charles D. Lennox, Hudson, N.H.; Troy W. Roberts, Arlington, Mass.

[73] Assignee: Boston Scientific Corporation, Watertown, Mass.

[21] Appl. No.: 105,737

[22] Filed: Aug. 12, 1993

[51] Int. Cl.$^6$ ............................................. A61M 31/00
[52] U.S. Cl. ...................................... 604/53; 604/101; 604/113; 606/28; 607/101
[58] Field of Search ............... 604/49, 53, 96, 101, 604/113–114; 606/27, 28, 31, 192, 194; 607/96, 101, 104–105

[56] References Cited

U.S. PATENT DOCUMENTS

| | | | |
|---|---|---|---|
| 4,610,662 | 9/1986 | Weukl et al. | 604/53 |
| 4,744,366 | 5/1988 | Jang | 128/344 |
| 4,773,413 | 9/1988 | Hussein et al. | 128/303 |
| 4,799,479 | 1/1989 | Spears | 128/303 |
| 4,824,436 | 4/1989 | Wolinsky | 604/53 |
| 4,832,688 | 5/1989 | Sagae et al. | 604/53 |
| 5,019,075 | 5/1991 | Spears et al. | 606/7 |
| 5,041,089 | 8/1991 | Mueller et al. | 604/96 |
| 5,045,056 | 9/1991 | Behl | 604/49 |
| 5,135,484 | 8/1992 | Wright | 604/28 |
| 5,151,100 | 9/1992 | Abele et al. | 606/28 |
| 5,190,540 | 3/1993 | Lee | 606/28 |
| 5,219,355 | 6/1993 | Parodi et al. | 606/191 |

Primary Examiner—Corrine Maglione
Attorney, Agent, or Firm—Pearson and Pearson

[57] ABSTRACT

An apparatus and method for treating an aneurysm in a vessel that isolates a volume around the aneurysm, evacuates that volume and heats the aneurysmal wall. A catheter includes one or more inflatable balloons for defining the isolated volume and occluding and preventing any blood flow through the volume. Suction applied through the catheter to the isolated volume withdraws any blood in the isolated volume and displaces the tissue for contact with a thermal source that heats the aneurysmal wall. When the treatment is completed, the balloons are deflated and the catheter is removed from the vessel.

13 Claims, 3 Drawing Sheets

METHOD FOR TREATING ANEURYSMS WITH A THERMAL SOURCE

BACKGROUND OF THE INVENTION

1. Field of the Invention

This invention generally relates to the treatment of aneurysms and more specifically to a method and apparatus for treating aneurysms.

2. Description of Related Art

Aneurysms, as known, are abnormal dilatations of a vessel caused by weakening of the vessel's wall that can occur anywhere in the body. Most commonly aneurysms occur in cerebral and aortic vessels, and they must be treated to avoid rupture and hemorrhage.

Conventional treatment involves the placement of clips on the aneurysm during a surgical procedure. The clips essentially gather the weakened aneurysmal wall to prevent its exposure in its weakened state to the pressure exerted by and flow dynamics of blood in the vessel. Such surgery involves patient risk and trauma and foreign objects, such as the clips, remain in the patient's body.

U.S. Pat. No. 5,219,355 to Parodi et al. discloses a balloon device for implanting an aortic or aortodiiliac intraluminal prothesis for repairing aneurysms. The device includes a catheter having two inflatable balloons for expanding two stents associated with a tube extending through the vessel internally of and in parallel to the aneurysm. When the prothesis is properly located, the balloons inflate and expand the stents into contact with normal vessel wall portions adjacent the aneurysm to clamp the tube in place. The tube provides a continuous passage through the dilatation and eliminates the application of pressure to the weakened aneurysmal wall. The tube and the stents remain in the patient after the balloons are deflated and withdrawn with the catheter. This balloon device is described for the treatment of aortic aneurysms. It does not appear reasonable to apply this approach to cerebral aneurysms where the vessels are significantly smaller than aortic vessels. Moreover, the apparatus is disclosed for the repair of aneurysms that form in a single passage vessel. In many cases, however, an aneurysm forms at a bifurcation in the vessel system where a single passage may divide into two or more passages. Such apparatus would not appear adapted to the treatment of such aneurysms.

U.S. Pat. No. 4,832,688 to Sagae et al. discloses a multi-lumen catheter for the repair of a ruptured blood vessel. In one embodiment, the catheter carries two axially spaced occlusion balloons and an intermediate clamping balloon that is positioned proximate a tear in a vessel wall. The catheter additionally includes a lumen for injecting a therapeutic agent, such as heparin, between the occlusion balloons. In use, the occlusion balloons inflate to isolate a volume around the rupture in the vessel wall. After heparin is administered, the middle balloon expands to hold the ruptured wall in position until the repair is effected. After some time interval, all the balloons are deflated and the catheter is removed from the patient.

U.S. Pat. No. 5,019,075 to Spears et al. discloses a thermal balloon for heating surrounding tissue, particularly in connection with percutaneous transluminal coronary angioplasty. Heating fuses together fragmented segments of tissue and coagulates blood trapped within dissected planes of the tissue and within fissures created by any wall fractures. This activity prevents the collapse of any flap of material that could cause either abrupt arterial closure or gradual restenosis at the site of the treatment.

Both the Sagae et al. and Spears et al. patents disclose apparatus for use in percutaneous transluminal angioplasty. Neither, however, suggests any use of their respective devices or apparatus in the treatment of aneurysms.

SUMMARY

Therefore, it is an object of this invention to provide a method and apparatus for treating aneurysms.

Another object of this invention is to provide a method and apparatus for the percutaneous treatment of aneurysms.

Still another object of this invention is to provide a method and apparatus for treating aneurysms located in cerebral blood vessels.

Yet still another object of this invention is to provide a method and apparatus for treating an aneurysm at a vessel bifurcation.

In accordance with one aspect of this invention, an aneurysm in a vessel is treated by first isolating, with at least one percutaneously administered expansible balloon, a volume in the vessel around the aneurysm. The pressure in the isolated volume is then reduced to evacuate any blood and to displace the weakened aneurysmal wall toward its original location. Heating of the weakened aneurysmal wall thickens and strengthens it. After heating, the vessel is cleared to allow normal blood flow to recur.

In accordance with another aspect of this invention, apparatus for treating an aneurysm includes a catheter that is guided to the site of the aneurysm. The catheter carries at least one expansible balloon for defining an isolated volume in the vessel around the aneurysm. A displacement structure communicates with the isolated volume and displaces the aneurysmal wall for contact with a heater associated with the catheter. The heater thermally coagulates the displaced weakened aneurysmal wall thereby to thicken and strengthen the wall and repair the aneurysm.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
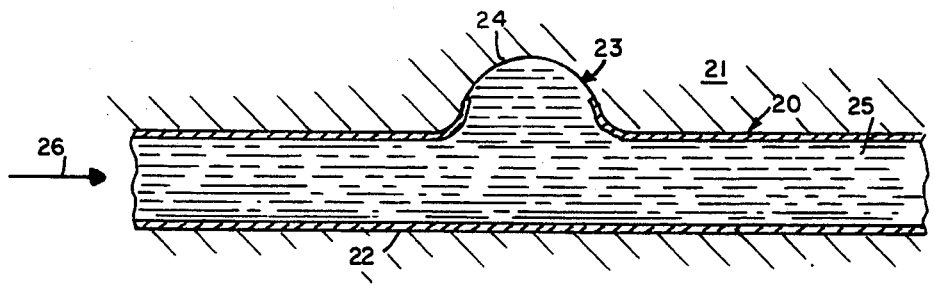
FIG. 1 depicts a single passage vessel with an aneurysm.

FIG. 1 depicts, in simplified form, a single-passage, tubular vessel 20 through tissue 21, such as peri-arterial tissue, defined by a vessel wall 22. Although FIG. 1, and the other figures, depict a vessel wall as comprising a single homogeneous layer, it will be recognized that an actual vessel wall has multiple layers. However, this invention can be understood by referring to the simplified, homogenous representation in the figures.

FIG. 1 illustrates an aneurysm 23 in the vessel wall that is an abnormal dilatation of the blood vessel 20 due to weakening and stretching of an aneurysmal wall 24 in otherwise normal wall portions 22. Blood 25 flows in a direction represented by arrow 26 within the vessel 20. If left untreated, the aneurysm 23 can grow in size, rupture and allow hemorrhaging of blood 25 from the vessel 20 into the surrounding tissue 21.

Figure 2:
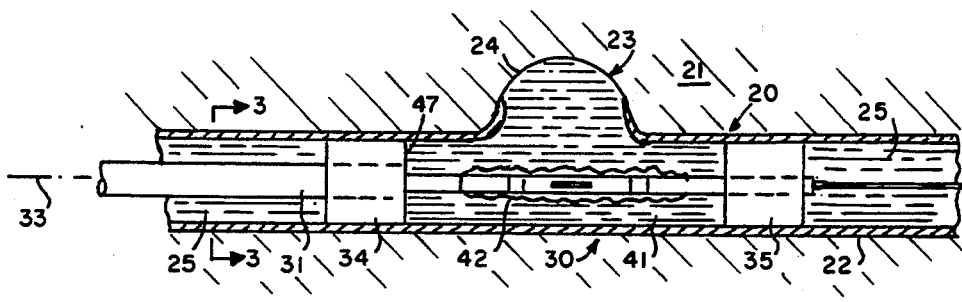
FIG. 2 discloses one form of apparatus constructed in accordance with this invention for treating the aneurysm in FIG. 1 at a first stage in a treatment modality.

FIG. 2 depicts one embodiment of apparatus 30 constructed in accordance with this invention that includes a catheter 31 positioned over a percutaneously administered guidewire 32. The catheter 31 extends generally along an axis 33 and supports a proximal occlusion balloon 34 and an axially spaced distal occlusion balloon 35.

Figure 3:
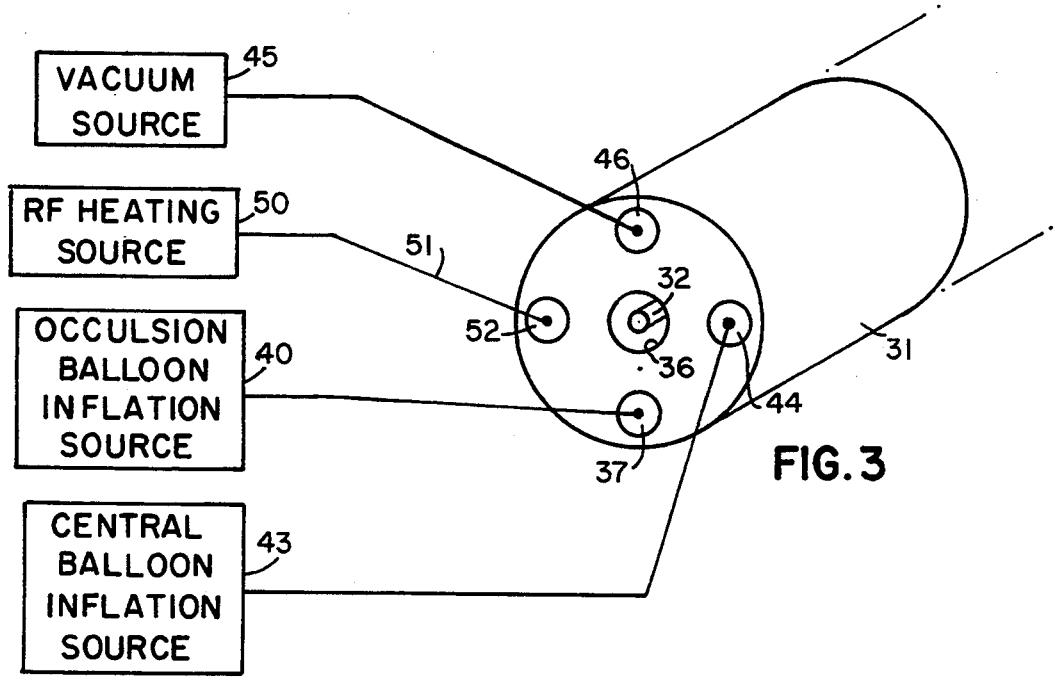
FIG. 3 is a view, partly in schematic and partly in perspective form of portions of the apparatus taken along lines 3—3 in FIG. 2.

Referring to FIGS. 2 and 3, the catheter 31 also includes a central guidewire lumen 36 and an occlusion balloon inflation lumen 37 that connects to an occlusion balloon inflation source 40. FIG. 2 depicts the apparatus 30 after the occlusion balloon inflation source 40 in FIG. 3 expands the balloons 34 and 35 in the vessel 20 into normal portions of the wall 25 proximally and distally of the aneurysm 23. The occlusion balloons 34 and 35 thereby define an isolated volume 41 in the vessel 20 around the aneurysm 23.

Referring again to FIGS. 2 and 3, the catheter 31 additionally supports a central balloon 42 (FIG. 2) shown in a collapsed form. A central balloon inflation source 43 (FIG. 3) inflates the central balloon 42 through a lumen 44 in the catheter 31.

Figure 4:
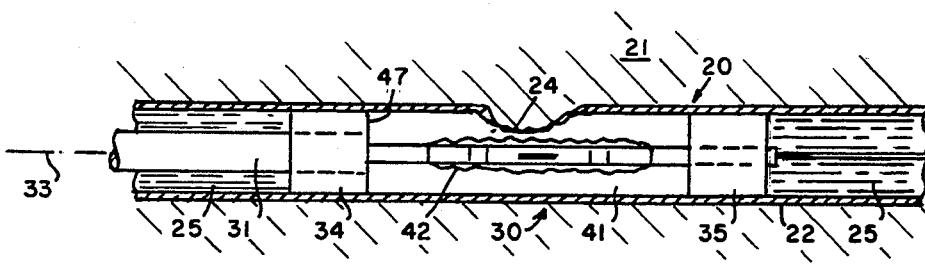
FIG. 4 depicts the apparatus in FIG. 2 at an intermediate stage of the treatment modality.

A vacuum source 45 (FIG. 3) connects to a suction lumen 46 that terminates at a port 47 (FIG. 2) located distally of the proximal occlusion balloon 34. Alternatively, the port can exit the catheter 31 at any location intermediate the occlusion balloons 34 and 35. When the vacuum source 45 applies suction to the lumen 46, it draws blood 25 through the lumen 46 to evacuate the isolated volume 41. Simultaneously, the aneurysmal weakened wall 24 displaces toward the catheter 31 and the center axis 33 as shown in FIG. 4. At this point in the sequence, the occlusion balloons 34 and 35 are still expanded to define the isolated volume 41. The central balloon 42 is deflated, and blood is left within the isolated volume 41. The aneurysmal wall 24 has collapsed from a convex orientation as shown in FIG. 2 to a concave orientation as shown in FIG. 4.

Figure 5:
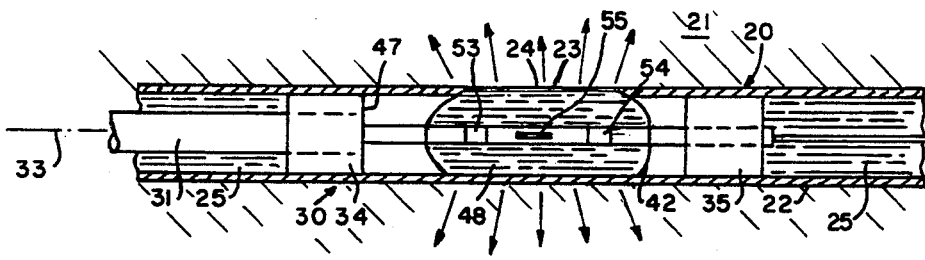
FIG. 5 depicts the apparatus of FIG. 2 at final stage of the treatment modality.

As a next step in the treatment modality and as shown in FIG. 5, the central balloon inflation source 43 (FIG. 3) inflates the central balloon 42 through the lumen 44 to expand the aneurysmal wall 24 into a position where it essentially constitutes a continuation of the normal wall portions of the vessel wall 22. This inflation occurs when the central balloon inflation source pumps an ionizable liquid 48 into the central balloon 42.

After this positioning occurs, an rf heating source 50, with conductors 51 carried in a lumen 52 energizes spaced electrodes 53 and 54 on the catheter 31 internally of the central balloon 42. The resulting current between the electrodes 53 and 54 heats the liquid 48 within the central balloon 42 and the surrounding tissue including the weakened aneurysmal wall 24. This heat thermally coagulates the weakened aneurysmal wall 24. Specifically, thermal coagulation has the chronic effect of forming fibrous scar tissue in the weakened aneurysmal wall 24. This shrinks and thickens the aneurysmal wall 24 to reduce its compliance and arrest progression of the aneurysm formation.

During the heating process, a temperature sensor 55 that connects through the conductors 51 to the rf heating source 50 shown in FIG. 3, provides a feedback control signal. Thus the rf heating source can accurately regulate the temperature of the liquid 48.

Figure 6:
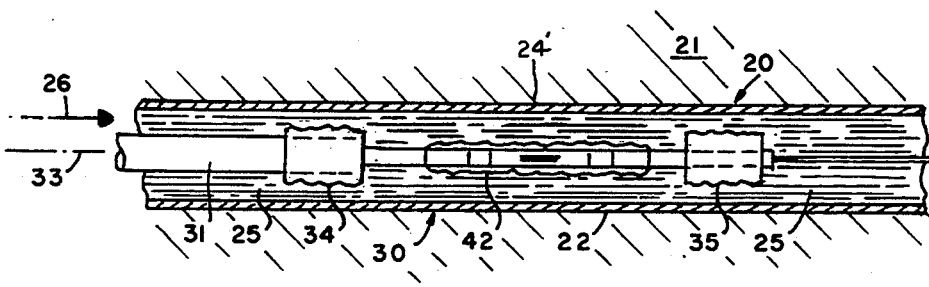
FIG. 6 depicts a repaired vessel and the apparatus and the apparatus of FIG. 1 prior to its removal from the vessel.

When the treatment is completed, the RF heating source 50 deenergizes, the vacuum source 45 turns off, the central balloon inflation source 43 deflates the central balloon 42 and the occlusion balloon inflation source 40 deflates the occlusion balloons 34 and 35. This results in the apparatus assuming a compacted form as shown in FIG. 6. Blood 25 then flows through the vessel 20 in the direction of the arrow 26 past the apparatus 30. Next a surgeon removes the apparatus 30 simultaneously with or sequentially before the guidewire 32 leaving a vessel 20 with a thickened and strengthened wall portion 24' in place of the thin, stretched, weakened wall 24 in FIG. 1.

The specific apparatus 30 in FIGS. 1 through 6 includes a catheter 31 with five discrete lumens. Certain functions of these lumens may be combined in a single lumen. For example, the vacuum source 45 might connect directly to the guidewire lumen 36 to evacuate the blood 25 in the isolated volume 41 through the lumen 36 over the guidewire 32. Other such functional combinations are also possible. In addition, each of the individual components including the occlusion balloons 34 and 35 and the central balloon 42 have conventional constructions. Apparatus for heating the liquid 48 in the balloon 42 through the use of RF energy applied to electrodes 53 and 54 and related systems including the temperature sensor 55 are also known in the art. Thus it will be apparent that the apparatus 30 shown in FIGS. 2 through 6 is readily manufactured. Moreover, the operating techniques are analogous to standard medical procedures with respect to positioning the catheter 31 in the blood vessel 20, inflating the individual balloons and heating the liquid. However, the apparatus 30 in FIGS. 2 through 6 provides advantages over prior art systems. The need for surgery for the installation of clips with its attendant risk and trauma is eliminated. No foreign objects, such as clips or tubes, remain in the patient after treatment. The configuration allows the catheter and balloons to be sized for the treatment of aneurysms in both aortic and cerebral vessels.

Figure 7:
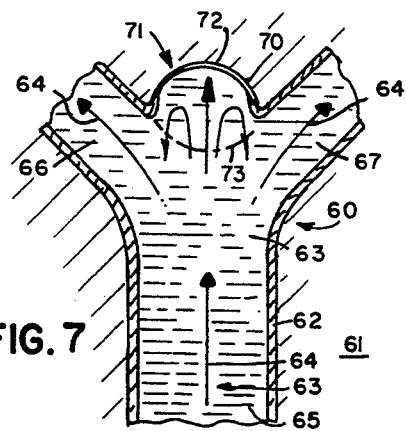
FIG. 7 depicts a vessel with bifurcated passages and an aneurysm at the bifurcation.

As previously indicated, FIG. 1 depicts an aneurysm 23 formed in a single passage vessel 20. In many situations, however, the aneurysm forms at a branch in a vessel as shown in FIG. 7. FIGS. 8 through 12 depict such a vessel and an apparatus specifically adapted for treating an aneurysm at a bifurcation in that vessel.

FIG. 7 depicts a bifurcated vessel 60 formed through tissue 61 and bounded by a vessel wall 62. Blood 63 flows along lines 64 up a main trunk 65, to split into parallel passages 66 and 67. As shown, an aneurysm 70 is formed as a dilatation of the vessel 60 at the bifurcation 71 by a thin or weakened aneurysmal wall 72. The pressure acting on the aneurysmal wall 72 expands the vessel from a position shown by a dashed line 73 corresponding to the original wall position.

Figure 8:
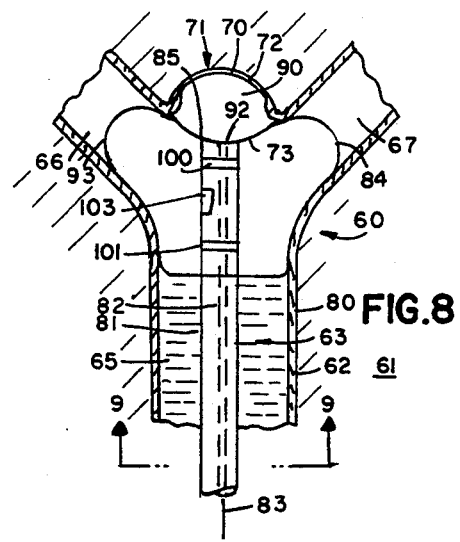
FIG. 8 discloses another form of apparatus constructed in accordance with this invention for treating the aneurysm shown in FIG. 7 at a first stage in a treatment modality.

In FIG. 8 an aneurysm treatment apparatus 80 has been positioned percutaneously in the vessel 60 by means of a catheter 81 installed over a guidewire 82 (shown by phantom). The catheter 31 extends generally along a vertical axis 83 as shown in FIG. 8 and supports a compliant balloon 84 extending proximally from a distal end 85 of the catheter 81. The distal end 85 is positioned at the site of original wall position represented by the dashed line 73.

Figure 9:
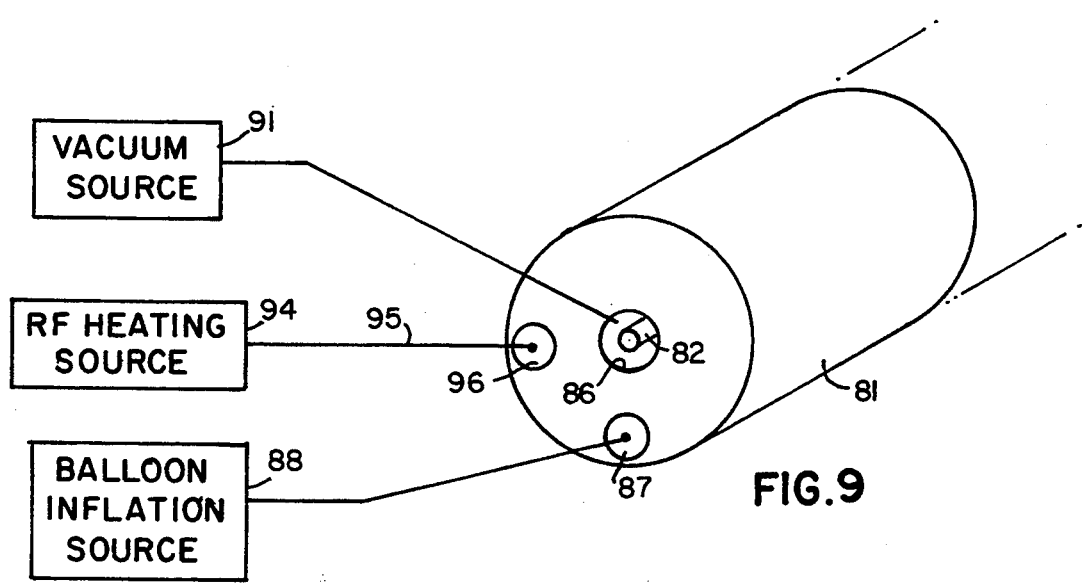
FIG. 9 is a view, partly in schematic and partly in perspective form of portions of the apparatus taken along lines 9—9 in FIG. 8.

Referring to FIG. 9, the catheter 81 includes a first lumen 86 that slides over the guidewire 82. A second lumen 87 connects to a balloon inflation source 88 and exits at the distal region of the catheter 31 within the confines of the compliant balloon 84. When the balloon inflation source 88 expands the balloon 84 as shown in FIG. 8, it occludes the vessel 60 by blocking the main trunk 65 and the passages 66 and 67. Alternatively, the compliant balloon 84 could expand to occlude only the main trunk 65 and form a seal around the aneurysmal wall 72 with the healthy tissue of the vessel 60 without blocking the passages 66 and 67. In either embodiment, the compliant balloon 84 defines an isolated volume 90 in the vessel 60 adjacent the distal end 85 of the catheter 81 and around the aneurysm 70.

Figure 10:
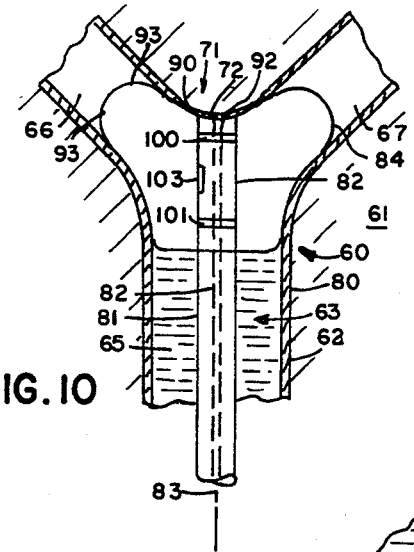
FIG. 10 depicts the apparatus in vessel of FIG. 8 at an intermediate stage of the treatment modality.

Referring to FIGS. 8 and 9, the catheter 81 additionally connects to a vacuum source 91. In this particular embodiment, the vacuum source 91 draws suction through the central lumen 86 to draw blood 63 in the volume 90 through a port 92 formed at the distal end 85 of the catheter 81. The suction additionally reduces the pressure in the isolated volume 90 so the aneurysmal wall 72 displaces toward the distal end 85 of the catheter 81 as shown in FIG. 10.

As the compliant balloon 84 inflates, it forms a surface 93 facing the aneurysm 70 generally along the original position of the weakened wall 72 as represented by the dashed line 73. As shown in FIG. 10, the evacuation, therefore, tends also to pull the aneurysmal wall 72 towards the distal end 85 of the catheter 81 for contact with the surface 93. Thus the aneurysmal wall 72 tends to assume its original orientation in the vessel 60.

Figure 11:
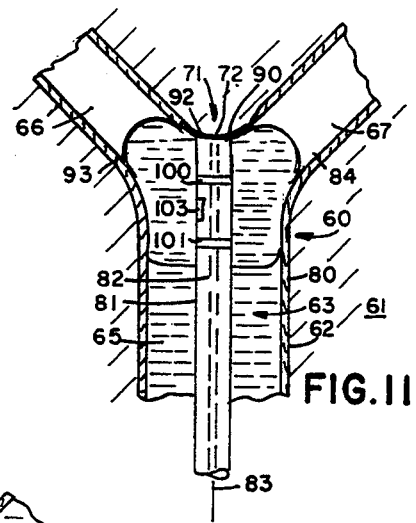
FIG. 11 depicts the apparatus of FIG. 8 at a final stage of the treatment modality.

With the vacuum source 91 energized, an RF heating source 94 including conductors 95 in a lumen 96 energizes axially spaced electrodes 100 and 101 as shown in FIG. 11. More specifically, the balloon inflation source 88 inflates the compliant balloon 84 by pumping an ionizable liquid into the balloon 84. A temperature sensor 103 connects back to the RF heating source 94 through additional conductors 95 to enable accurate temperature regulation of the liquid 102. Consequently, the rf energy heats the liquid 102 to a regulated temperature. As previously indicated, this heating produces thermal coagulation of the aneurysmal wall 71 with the chronic effect of forming fiber scar tissue that reduces the compliance at the aneurysm 70 and arrests progression of the aneurysm formation.

Figure 12:
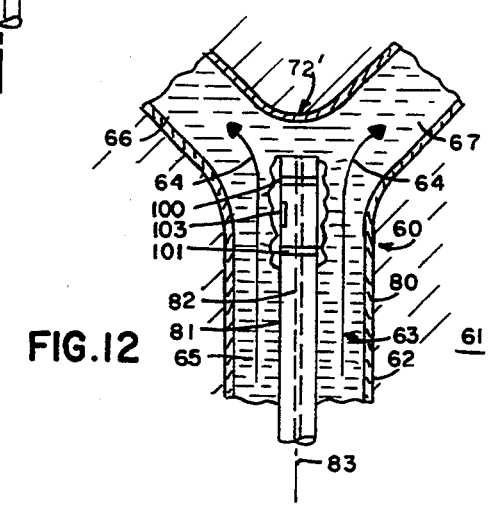
FIG. 12 depicts a repaired vessel and the apparatus of FIG. 8 prior to its removal from the vessel.

When the coagulation is complete, the RF heating source 94 and the vacuum sources 91 turn off. The balloon inflation source 88 allows the balloon 84 to collapse to a compact position as shown in FIG. 12. The vessel wall 62 has a thickened and strengthened wall 72' at the location of the aneurysmal wall. In this orientation with a reduced balloon volume, a surgeon can readily remove the catheter 81, with the balloon 84, and the guidewire 82 from the patient simultaneously or in sequence.

In accordance with the embodiment of this invention shown in FIGS. 8 through 12, a catheter 81 carries a single compliant balloon 84 at its distal end 85 for producing an isolated volume 91 around an aneurysm 70. Evacuating the isolated volume 91 removes any blood 63 and draws the aneurysmal wall 72 into a position approximating its original position for bearing against the surface 93. Heat applied through the compliant balloon thermally coagulates the aneurysmal wall. As with the apparatus shown in FIGS. 2 through 6, foreign objects do not remain in the patient after treatment with the apparatus 80.

As will now be apparent, this invention has been disclosed in two distinct embodiments disclosed in FIGS. 2 through 6 and in FIGS. 8 through 12 that have certain common features. In both the apparatus defines an isolated volume around an aneurysm. In both suction evacuates this volume, thereby removing any blood from the isolated volume and displacing the aneurysmal wall. In both, heat applied to the aneurysmal wall thermally coagulates the wall to thicken and strengthen it and reduce its compliance. It will also be apparent that each apparatus is constructed of conventional components that can be manufactured by conventional processes.

It will be apparent, however, that many modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. A method for treating an aneurysm in the wall of a vessel defined by an aneurysmal wall with adjacent normal wall portions, said method comprising the steps of:
   A. isolating, with a percutaneously administered expansible means, a volume in the vessel around the aneurysm,
   B. reducing the pressure in the isolated volume through evacuating means carried with the expansible means thereby to evacuate the isolated volume and displace the aneurysmal wall,
   C. heating the aneurysmal wall with heating means carried with the expansible means thereby to thicken and strengthen the aneurysmal wall, and
   D. clearing the vessel by removing the expansible means, the evacuating means and the heating means.

2. A method as recited in claim 1 wherein said isolating step comprises the steps of directing a catheter carrying the expansible means including an expansible balloon to the site of the aneurysm and inflating the balloon into the normal wall portions thereby to occlude the vessel.

3. A method as recited in claim 2 wherein said pressure reducing step includes applying a vacuum through the evacuating means which includes a lumen in the catheter that communicates with a port positioned in the isolated volume thereby to evacuate the isolated volume and displace the aneurysmal wall for contact with the heating means.

4. A method as recited in claim 3 wherein heating step includes the step of supply heated liquid to the balloon thereby to heat the displaced tissue contacting the balloon.

5. A method as recited in claim 4 wherein said step of clearing the vessel includes the steps of discontinuing said heating, removing the vacuum and deflating the balloon.

6. A method as recited in claim 1 wherein said step of isolating the volume around the aneurysm includes positioning a steerable guidewire in the vessel with its distal end past the aneurysm and introducing a catheter over the guidewire, which catheter extends from a proximal end to a distal end and supports the expansible means and a port of the evacuating means at its distal end.

7. A method as recited in claim 6 wherein said step of reducing pressure in the isolated volume includes applying a vacuum at the proximal end of the catheter through a lumen of the evacuating means in the catheter that communicates with the port thereby to evacuate the isolated volume and displace the aneurysmal wall for contact with the heating means.

8. A method as recited in claim 7 wherein the method is used to repair an aneurysm at a vessel bifurcation formed at the juncture of a first, second and third vessels and said step of isolating the volume around the aneurysm includes inflating the expansible means, which includes at least one balloon, in the juncture thereby to occlude the first, second and third vessels.

9. A method as recited in claim 8 wherein said inflating step includes filling the balloon with a liquid from a balloon inflation source at the proximal end of the catheter through a balloon inflation lumen in the catheter that exits the catheter at its distal end interiorly of the balloon and said heating step includes heating the liquid in the balloon.

10. A method as recited in claim 8 wherein said inflating step includes filling the balloon with a ionizable liquid from a balloon inflation source at the proximal end of the catheter through a balloon inflation lumen in the catheter that exits the catheter at its distal end interiorly of the balloon and said heating step includes applying radio frequency energy to the liquid in the balloon thereby to heat the liquid in the balloon.

11. A method as recited in claim 7 wherein the method is used to repair an aneurysm at a tubular vessel and said step of isolating the volume around the aneurysm includes locating the expansible means comprising axially spaced occlusion balloons in the vessel proximally and distally of the aneurysm and inflating the occlusion balloons from an occlusion balloon inflation source at the proximal end of the catheter through an occlusion balloon lumen that extends through the catheter and exits the catheter at its distal end within the occlusion balloons thereby to expand the occlusion balloons into normal wall portions adjacent the aneurysm to occlude the vessel proximate the aneurysm.

12. A method as recited in claim 11 wherein the catheter includes a thermal balloon intermediate the occlusion balloons and said heating step includes inflating the thermal balloon with a liquid from a thermal balloon inflation source at the proximal end of the catheter through a thermal balloon inflation lumen in the catheter that exits the catheter at its distal end interiorly of the thermal balloon and heating the liquid in the thermal balloon.

13. A method as recited in claim 11 wherein the catheter includes a thermal balloon intermediate the occlusion balloons and said heating step includes inflating the thermal balloon with an ionizable liquid from a thermal balloon inflation source at the proximal end of the catheter through a thermal balloon inflation lumen in the catheter that exits the catheter at its distal end interiorly of the thermal balloon and applying radio frequency energy to the liquid in the thermal balloon thereby to heat the liquid in the thermal balloon.

* * * * *